(12) United States Patent
Lorkovic

(10) Patent No.: US 8,278,493 B2
(45) Date of Patent: Oct. 2, 2012

(54) HYDROCARBON SYNTHESIS

(75) Inventor: Ivan M. Lorkovic, Santa Barbara, CA (US)

(73) Assignee: GRT, Inc., Santa Barbara, CA (US)

( * ) Notice: Subject to any disclaimer, the term of this patent is extended or adjusted under 35 U.S.C. 154(b) by 5 days.

(21) Appl. No.: 13/107,611

(22) Filed: May 13, 2011

(65) Prior Publication Data

US 2011/0218375 A1     Sep. 8, 2011

Related U.S. Application Data

(63) Continuation of application No. 12/683,607, filed on Jan. 7, 2010, now Pat. No. 7,964,764, which is a continuation of application No. 12/080,594, filed on Apr. 3, 2008, now abandoned, which is a continuation of application No. 11/091,130, filed on Mar. 28, 2005, now abandoned, which is a continuation-in-part of application No. 10/893,418, filed on Jul. 15, 2004, now abandoned.

(60) Provisional application No. 60/487,364, filed on Jul. 15, 2003.

(51) Int. Cl.
*C07C 1/00* (2006.01)
(52) U.S. Cl. ........ 585/359; 585/408; 585/469; 585/642; 585/733; 585/943; 585/935
(58) Field of Classification Search .................. None
See application file for complete search history.

(56) References Cited

U.S. PATENT DOCUMENTS

| | | | |
|---|---|---|---|
| 7,348,464 B2 * | 3/2008 | Waycuilis | 585/408 |
| 7,964,764 B2 | 6/2011 | Lorkovic et al. | |
| 2003/0078456 A1 * | 4/2003 | Yilmaz et al. | 568/488 |
| 2003/0166973 A1 * | 9/2003 | Zhou et al. | 568/488 |
| 2004/0267074 A1 * | 12/2004 | Grosso et al. | 585/618 |
| 2005/0234277 A1 * | 10/2005 | Waycuilis | 585/310 |
| 2006/0100469 A1 * | 5/2006 | Waycuilis | 585/324 |
| 2008/0275284 A1 * | 11/2008 | Waycuilis | 585/642 |
| 2011/0015458 A1 * | 1/2011 | Waycuilis et al. | 585/310 |
| 2012/0141356 A1 * | 6/2012 | Brickey et al. | 423/491 |

OTHER PUBLICATIONS

European Patent Office Communication for Application No. 04778505.0 dated Jun. 28, 2011.
Translation of Japanese Patent Office Communication for Application No. 2006-520386 dated Aug. 23, 2011.
Translation of Japanese Patent Office Communication for Application No. 2008-504198 dated Dec. 6, 2011.

* cited by examiner

*Primary Examiner* — Tam M Nguyen
(74) *Attorney, Agent, or Firm* — Baker Botts L.L.P.

(57) ABSTRACT

A method of synthesizing hydrocarbons from smaller hydrocarbons includes the steps of hydrocarbon halogenation, simultaneous oligomerization and hydrogen halide neutralization, and product recovery, with a metal-oxygen cataloreactant used to facilitate carbon-carbon coupling. Treatment with air or oxygen liberates halogen and regenerates the cataloreactant.

20 Claims, No Drawings

HYDROCARBON SYNTHESIS

CROSS-REFERENCE TO RELATED APPLICATION(S)

This application is a continuation of U.S. patent application Ser. No. 12/683,607, filed Jan. 7, 2010, now U.S. Pat. No. 7,964,764 which is a continuation of U.S. patent application Ser. No. 12/080,594, filed Apr. 3, 2008, now abandoned which is a continuation of Ser. No. 11/091,130, filed Mar. 28, 2005, now abandoned which is a continuation-in-part of U.S. patent application Ser. No. 10/893,418, filed Jul. 15, 2004, now abandoned which claims the benefit of U.S. Provisional Patent Application No. 60/487,364, filed Jul. 15, 2003.

FIELD OF THE INVENTION

This invention relates generally to hydrocarbon oligomerization, and more particularly to a method of making hydrocarbons using cataloreactants.

BACKGROUND OF THE INVENTION

Scientists have long sought efficient ways to convert methane and other alkanes into higher hydrocarbons, including light olefins and gasoline-range materials. Efficient processes could create value in a number of ways, including: facilitating the utilization of remotely located stranded natural gas through its conversion into more easily transportable liquid fuels and feedstocks, and allowing the use of inexpensive feedstocks (methane and other lower alkanes) for end products often made from higher alkanes, including ethylene and propylene.

U.S. Pat. Nos. 6,486,368, 6,472,572, 6,465,699, 6,465,696, and 6,462,243 disclose processes for converting alkanes into olefins, ethers, and alcohols. Many of the disclosed processes involve halogenation of an alkane, passing the halogenated products over a metal oxide to create products and metal halide, recovering the product(s), and regenerating the metal halide with oxygen or air to yield metal oxide and halogen for recycle to the process. Not described is alkane oligomerization: substantial coupling of the starting hydrocarbon to obtain product(s) of higher carbon number.

Several investigators have examined the use of halogenation for the production of higher hydrocarbons from methane. Representative patents include U.S. Pat. No. 4,513,092 (Chu), U.S. Pat. No. 4,769,504 (Noceti and Taylor), U.S. Pat. No. 5,087,786 (Nubel), and U.S. Pat. No. 6,452,058 (Schweitzer). As described in the Taylor patent: "Aromatic-rich, gasoline boiling range hydrocarbons [are made] from the lower alkanes, particularly from methane. The process is carried out in two stages. In the first, alkane is reacted with oxygen and hydrogen chloride over an oxyhydrochlorination catalyst such as copper chloride with minor proportions of potassium chloride and rare earth chloride. This produces an intermediate gaseous mixture containing water and chlorinated alkanes. The chlorinated alkanes are contacted with a crystalline aluminosilicate catalyst in the hydrogen or metal-promoted form to produce gasoline range hydrocarbons with a high proportion of aromatics and a small percentage of light hydrocarbons ($C_2$-$C_4$), as well as reforming the HCl. The light hydrocarbons can be recycled for further processing over the oxyhydrochlorination catalyst." All of these techniques for making higher alkanes from $C_1$ feedstocks suffer from the disadvantage that the hydrocarbon stream must be separated from an aqueous hydrohalic acid stream, and the hydrohalic acid stream must be recycled.

U.S. Pat. No. 4,795,843 (Tomotsu et al.) discloses a process for oligomerizing halomethanes to products including ethyl benzene, toluene, and xylenes, using silica polymorph or silicalite catalysts. The process does not incorporate reactive neutralization of hydrogen halide, and appears to suffer from slow kinetics.

In a process for halogenating hydrocarbons, Chang and Perkins noted trace amounts of oligomerization products in the presence of zeolites in U.S. Pat. No. 4,654,449. The oligomerization products were low in quantity, and generally halogenated.

U.S. Pat. No. 4,373,109 (Olah) discloses a process for converting heterosubstituted methanes, including methyl halides, by contacting such methanes with bifunctional acid-base catalysts at elevated temperatures, between 200 and 450 C, preferably between 250 and 375 C, to produce predominantly lower olefins, preferably ethylene and propylene. The catalysts of preference are those derived from halides, oxyhalides, oxides, sulfides or oxysulfides of transition metals of Groups IV, V, VI, VIII of the Periodic Table, such as tantalum, niobium, zirconium, tungsten, titanium, and chromium, deposited on acidic oxides and sulfides such as alumina, silica, zirconia or silica-alumina. Neither the use of solid oxide-based halogen recovery nor the formation of alcohols or ethers is disclosed. A related reference is "Ylide chemistry. 1. Bifunctional acid-base-catalyzed conversion of heterosubstituted methanes into ethylene and derived hydrocarbons. The oniuin-ylide mechanism of the C1→C2 conversion" by George A. Olah et al. (J. Am. Chem. Soc. 106, 2143 (1984)).

U.S. Pat. No. 3,894,107 (Butter, et al.) discloses improvements to a process for condensing halogenated hydrocarbons using zeolite catalysts. Notably absent is any discussion of solid oxide-based hydrogen halide neutralization.

Kochi has observed reductive coupling of alkyl halides when transition metal bromides are reacted with low-molecular weight Grignard reagents in THF or diethyl ether (Bulletin of the Chemical Society of Japan v. 44 1971 pp. 3063-73). Liquid phase chemistry, however, typically suffers from such disadvantages as the requirement of solvent, corrosion, and lower rates of reaction than gas-phase chemistry. In addition, such a process consumes energy required to produce the magnesium metal needed for the energetic and reducing Grignard reagents. This is not the same type of process as the dehydrohalogenative coupling and hydrogen halide neutralization we describe herein.

SUMMARY OF THE INVENTION

The present invention addresses the need for an efficient way to convert methane and other hydrocarbons into higher hydrocarbons. In one embodiment, a hydrocarbon having a carbon number $C_n$, where $n \geq 2$, is prepared by allowing a reactant hydrocarbon having a carbon number $C_m$, where $m < n$, to react with a halogenating agent, thereby forming a halogenated hydrocarbon; allowing the halogenated hydrocarbon to contact a metal-oxygen cataloreactant, thereby forming a product hydrocarbon having an carbon number $C_n$, where $n \geq 2$; recovering the product hydrocarbon; and regenerating the cataloreactant. Often, a mixture of hydrocarbons is obtained, but careful selection of the reactant hydrocarbon, halogenating agent, metal-oxygen cataloreactant, and reaction conditions allow a tailored approach to hydrocarbon product formation. Methane (i.e., natural gas) as well as other light hydrocarbons, e.g., $C_2$ to $C_6$ hydrocarbons, are envisioned as preferred feedstocks. More generally, the invention contemplates the use of feedstocks having carbon numbers as high as $C_{10}$. Laboratory observations have thus far focused on methane oligomerization and methyl bromide coupling, with detection of $C_2$-$C_{10}$ species, including alkanes, alkenes, branched hydrocarbons, and aromatic compounds.

DETAILED DESCRIPTION OF THE INVENTION

The present invention exploits the discovery that metal-oxygen compounds, such as mixed metal oxides, doped zeolites (i.e., alkaline-earth metal-doped zeolites), metal oxide-impregnated zeolites, etc., facilitate hydrocarbon oligomerization. According to one aspect of the invention, a hydrocarbon having a carbon number $C_n$, where $n \geq 2$, is formed by (i) forming a halogenated hydrocarbon by allowing a reactant hydrocarbon having a carbon number $C_m$, where $m < n$, to react with a halogenating agent; (ii) forming a product hydrocarbon having a carbon number $C_n$, where $n \geq 2$, by allowing the halogenated 5 hydrocarbon to contact a metal-oxygen cataloreactant; (iii) recovering the product hydrocarbon; and (iv) regenerating the cataloreactant.

More generally, the method entails the steps of halogenation, oligomerization, product recovery, and cataloreactant regeneration. The halogenated products may be separated from the unreacted (non-halogenated) hydrocarbon either before or after reaction with the metal-oxygen cataloreactant. Neutralization of any hydrohalic acid formed during the synthesis is advantageously accomplished concomitantly with carbon-carbon coupling and/or cataloreactant regeneration. Preferably, the process is an integrated one and takes place, for example, in a zone reactor, as described, for example, in U.S. Pat. No. 6,525,230 (Grosso), the entire contents of which is incorporated by reference herein. Thus, halogenation of methane or other hydrocarbons occurs within one zone of the reactor, and is followed by a condensation step in which the liberated hydrohalic acid is adsorbed within the same bifunctional material that catalyzes condensation of the halogenated hydrocarbon. Hydrocarbon oligomerization (defined as carbon-carbon coupling) takes place within this zone of the reactor and yields product hydrocarbons which, in general, will have carbon numbers ranging from $C_2$ to $C_{20}$, and may include alkanes, alkenes, alkynes, and/or aromatics. Treatment with air or oxygen liberates halogen for use in subsequent halogenation steps, and regenerates the cataloreactant material for subsequent condensation or metathesis. Advantageously, the need for recycling/recovering corrosive, aqueous hydrohalic acid is avoided because regeneration and recovery takes place in situ.

Higher hydrocarbon synthesis begins with a hydrocarbon feedstock: one or more reactant hydrocarbons, each having, independently, a carbon number $C_m$, where $m < n$, $C_n$ being the carbon number of the target hydrocarbon(s). Non-limiting examples of reactant hydrocarbons include methane, ethane, propane, etc., with natural gas (predominately methane, but often including small amounts of $C_2$ and higher species) being preferred. In general, the starting hydrocarbon has a carbon number between 1 and 10. Mixtures of hydrocarbons may also be used.

The reactant hydrocarbons are allowed to react with a halogenating agent. Non-limiting examples include molecular halogen (e.g., bromine, chlorine, etc.), alkyl halides (e.g., dibromomethane, bromoform, carbon tetrabromide), and condensed halides, such as metal bromides, which may be present as a solid, liquid, supported, or unsupported material.

Molecular halogens are preferred, with bromine ($Br_2$) being most preferred. Bromine is a liquid at room temperature, less reactive than chlorine and fluorine, and easy to handle. Bromine also has favorable energetics.

The reduction potential of bromine to bromide is 1.07 V vs. NHE, while that of oxygen to water is 1.23 V. A broad range of metal bromides may release bromine upon treatment with oxygen. At the same time, alkane bromination and subsequent alkyl bromide coupling and HBr neutralization are only mildly exothermic, but spontaneous enough to go to completion. Water and coupled hydrocarbons are the only fluid products. The same is not true with chlorine as mediator, for which HCl is a major component of the product stream. Hydrogen chloride production requires separation, drying, and recycling, which is costly. In short, the thermochemistry of metal bromide-mediated alkane partial oxidation is well-suited for efficient and inexpensive plant operation.

Halogenation of the reactant hydrocarbon may proceed in a number of ways, depending in part on the desired product(s) and in part on the feed. In one embodiment, an alkane is halogenated with molecular halogen using heat, light, or other electromagnetic radiation to drive the reaction, with heat being preferred. There is some benefit in having all steps—halogenation, oligomerization, and regeneration (described below)—occur at roughly the same temperature. For methanol to olefin (MTO) and methanol to gasoline (MTG) processes, temperatures of from 375 to 450° C. are utilized, with the range being important, if not critical. For the carbon-carbon coupling process described herein, an ideal temperature range, where all steps occur at roughly the same temperature, is 450 to 550° C.

However, individual reaction steps might be carried out at temperatures above or below this range. Indeed, gasoline yields are better at lower reaction temperatures and, in some of the examples below, the reaction of methyl bromide with an alkaline-earth metal-doped zeolite is carried out at a temperature of from 225 to 350° C. and a pressure of from 1 to 5 bar (14.5 to 72.5 psi). For a fully integrated process, however, the engineering favors running all three reactions at a similar temperature.

Halogenation preferably occurs at a pressure between 0.1 and 200 atm for the subsequent carbon-carbon step. Low pressure favors less carbon-carbon coupling (i.e., a smaller average molecular weight of product), while high pressure favors higher coupling. Processes for light olefins are likely to run at the same 60 to 200 psia that methanol to olefin (MTO) processes are run at, although higher pressures may alternatively be utilized. For production of gasoline-range molecules, pressures around 350 psia, as used in methanol to gasoline (MTG) processes, are envisioned. As a practical matter, running below atmospheric (more conservatively, below 2 psia) or above 100 atm is unlikely.

When molecular halogen is used as the halogenating agent, halogenation ideally is carried out at an alkane:halogen ratio of between 1:10 and about 100:1, on a volume by volume basis. At alkane:halogen ratios of less than 1:10 (i.e., more halogen), multi-halogenated hydrocarbons will be formed, typically leading to complete oxidation (i.e., $CO_2$) upon subsequent contact with the metal-oxygen cataloreactant. At alkane:halogen ratios higher than 100:1, the conversion to a halogenated hydrocarbon will be too low, perhaps 1% or less, and it is nearly impossible to imagine an economical process at such conversion levels. (30-60% conversion are more likely lower limits).

Altering the, ratio of halogen to alkane or other hydrocarbon feedstock may have a marked impact on product distribution. For example, one may choose to control the degree of halogenation in order to reduce aromatic formation in the production of lower olefins or fuels. A second example is minimizing formation of highly halogenated methane in order to reduce the formation of alkynes.

A key feature of the invention is the use of a metal-oxygen cataloreactant, which facilitates carbon-carbon coupling, i.e., hydrocarbon oligomerization. The term "metal-oxygen cataloreactant" is used herein to refer to a cataloreactant material containing both metal and oxygen. While not bound by theory, it is believed that the material catalyzes carbon-carbon coupling via hydrogen halide (e.g., HBr) elimination and alkylidene insertion into cationically activated C—H and possibly C—C bonds. The cataloreactant also acts as a halogen release and sequestering agent, and offers the possibility of obtaining a tunable coupling product distribution, including the ability to produce oxygenates if desired, while simultaneously trapping and recovering halogen, emitting only water as a byproduct. Treatment with air or oxygen regenerates the cataloreactant.

Nonlimiting examples of metal-oxygen cataloreactants include zeolites, doped zeolites, metal oxides, mixed metal oxides, metal oxide-impregnated zeolites, and similar materials, as well as mixtures of such materials. Nonlimiting examples of dopants include alkaline-earth metals, such as calcium and magnesium, and their oxides and/or hydroxides.

Zeolites are available from a variety of sources, including Zeolyst International (Valley Forge, Pa.). Specific examples include doped-ZSM-5 and doped mordenite (where, e.g., calcium and/or magnesium are the dopants).

Shifting the properties of the zeolite or zeolite component of a zeolite/metal oxide composite is also expected to shift product distribution. Pore size and acidity are particularly expected to be important. Acidity may be used to control chain length and functionality, and pore size may control chain length and functionality. Zeolites of particular pore-size may, selectively produce benzene, toluene, para-xylene, ortho-xylene, meta-xylene, mixed xylenes, ethyl benzene, styrene, linear alkyl benzene, or other aromatic products. The use of pore size is not limited to aromatic products.

In one embodiment of the invention, a metal oxide/zeolite composite is prepared by mixing a zeolite with a metal nitrate (e.g., an alkaline-earth metal oxide, such as calcium nitrate) or hydrated species thereof, and then calcining this mixture to release nitrogen oxides and retain the metal oxide-impregnated zeolite.

After oligomerization, the metal-oxygen cataloreactant is regenerated by treatment with air or oxygen, typically at a temperature of from 200 to 900° C. This converts metal halide species into metal-oxygen species.

A number of variables, including feed composition, feed location in the reactor, temperature, pressure, metal oxide composition, and reactor residence time may alter the product distribution. Production of alkanes, olefins and aromatics from methane has been detected and confirmed. Also expected is the ability to produce alkanes and olefins of particular branching (including mono-methyl branched alcohols), alcohols, diols, ethers, halogenated hydrocarbons, aromatics including benzene, styrene, ethyl benzene, toluene, xylenes, and linear alkyl benzenes, and hydrocarbons suitable for fuels such as gasoline, diesel, and jet fuel.

Control of the feed composition can control the product distribution. First, hydrogen halide produced in the halogenation may be neutralized (to form water or alcohol) with the same metal-oxygen compound producing the hydrocarbon product(s), or with a separate metal-oxygen compound in a distinct reactor. Shifting the hydrogen halide neutralization location may shift the product distribution, including functionality, chain length, and branching. For example, concurrent neutralization and product formation may be expected to drive the production of alcohols, which may or may not undergo further reactions such as coupling or dehydration. Second, water addition to the feed may shift product distribution. In particular, the addition of water may favor alcohol products. The addition of water may also control degree and type of branching and chain length. Third, hydrogen addition may alter the product distribution. Hydrogen may increase alkanes at the expense of other functionalities, something particularly useful for producing fuels. Hydrogen may also reduce coking and help control the chain length and branching.

It will also be appreciated that carbon-carbon oligomerization may proceed by a number of pathways. Even single-hydrocarbon feedstocks may yield more than one product. On the other hand, in one embodiment of the invention, controlled halogenation is used to produce predominately one isomer in favor of another (e.g., selective formation of 1-butene or 2-butene). Mixed feedstocks, such as raw natural gas, may give rise to oligomerization of multiple halogenated hydrocarbons (e.g., ethyl halide, dihaloethane, methyl halide, methyl dihalide, propyl halide, propyl dihalide, etc.). Indeed, in one embodiment of the invention, an alkyl halide is purposefully introduced to create desired branched products. An example would be oligomerization of methyl halide (from methane) with ethyl halide or a higher alkyl halide to produce, selectively, methyl, ethyl, propyl, isopropyl, or tertiary butyl (or other) branching. Another example might be the synthesis of styrene from ethyl halide, methyl halide, and dihalomethane.

In one embodiment of the invention, the reaction of halogenated hydrocarbon with a metal-oxygen cataloreactant takes place in a fluidized bed. Alternatively, a fixed bed is employed. Different alkyl halides may be introduced at different locations in the reactor. One example is the introduction of methyl halides at one location in a reactor to produce benzene, to which ethyl halides are added, producing styrene or ethyl benzene. Another example is the introduction of methyl halides at one location in a reactor to produce benzene, to which alkyl halides are added, producing linear alkyl benzene.

Product separation is accomplished by any suitable method. Nonlimiting examples include distillation, adsorption, and extraction. Product(s) may be recovered from the solid by stripping with steam, carbon dioxide, or other means.

The following are nonlimiting examples of the invention:

EXAMPLE 1

Metal Oxide/Zeolite composite MZ1 was prepared as follows: A solid mixture of a ZSM-5-type zeolite (Zeolyst CBV 8014, Si/Al ratio=80:1, 10 g, 170 mmoles $SiO_2$) and $CaNO_3$ nonahydrate (9 g, =34 mmoles Ca) was prepared and water was added to incipient wetness. After $CaNO_3$ dissolution and stirring, the slurry was dried and calcined in sequence at 115° C. (overnight) and 500° C. (overnight), respectively, in air.

EXAMPLE 2

Methane at 15 psia was bubbled through bromine at 1 ° C. at a rate of 5 cc/min. The resulting stream of bromine and methane (1:10 by mole) was passed through a small diameter bromination reactor at 450° C. ($1000 h^{-1}$) and the mixture of $CH_{4-x}Br_x$ (x=0, 1, 2, 3) passed into a reactor containing 5 g of metal oxide/zeolite composite MZ1 (400 C). The output stream from the second reactor contained no brominated products. Based on the methane consumed in the bromination reactor, 10% ethylene, 31% propylene, 3% propane, and 21% butanes/butenes were detected; 65% overall. Trace amounts of $C_6$ species were also detected. After reaction for 5 hours, during which the stream output did not change from the distribution described above, the methane stream was discontinued and the reactor was purged with helium at 5 cc/min for 10 minutes. After He purge, a flow of $O_2$ (2 cc/min) into the second reactor was initiated at 525 C to regenerate the metal oxide from the metal bromide of the partially spent composite. Initially only water and $CO_2$ were observed as products, but abruptly the stream contents changed to $Br_2$ and unreacted $O_2$. After 1 hour, the $O_2$ purge was discontinued and the reactor was again purged with helium. The caustic trap used during regeneration was tested for $CO_3^{-2}$ and 1.0 mmol was found, representing 24% of the converted carbon. The remainder of carbon was found to be higher boiling volatile aromatics (mostly toluene, xylenes and mesitylenes). A second cycle of bromomethanes condensation as described above was initiated at 400° C. and the product distribution was found to be identical to the first run. Three more cycles of condensation/neutralization/regeneration produced the same output of higher hydrocarbons.

EXAMPLE 3

A doped mordenite (Zeolyst CBV 21A, doped with both Ca and Mg) (5 g) was prepared according to Example 1, and used as the cataloreactant in a hydrocarbon synthesis substantially similar to that described above in Example 2. The product output was 30% ethylene, 5% ethane, 10% propylene, 3% propane, 5% butanes/butenes. Multiple runs and cataloreactant regeneration established reproducibility.

EXAMPLES 4-15

A ZSM-5-type zeolite (Zeolyst CBV 28014, having a 280:1 Si:Al ratio) from Zeolyst Corp. was doped with calcium according to the procedure described in Example 1, to a 4:1 Ca:Si ratio. A glass reaction tube (6 in. length; 4 mm inner diameter) was charged with 1.427 g of the coarsely ground, calcium-doped zeolite, and a stream of methyl bromide (4.5 mmol) was caused to flow into the tube. After conversion of methyl bromide, the solid was regenerated by treatment with $O_2$ (2 sccm, 1 bar) at 520 C) for 3 hours, and evolved $Br_2$ was recovered. The methyl bromide coupling reaction was performed over a range of pressures, temperatures, and flow rates using the same solid and same amount of methyl bromide per run. Products and any unreacted methyl bromide exited the opposite end of the reaction tube and were analyzed by one or more of GC, GC/MS, and NMR. Due to unmistakable isotope ratios and fragmentation patterns, GC/MS is particularly useful as a diagnostic of bromohydrocarbon content (which, typically, is zero).

Table 1 summarizes the hydrocarbon product distributions (also referred to as "selectivity" (sel), expressed as a percentage), percent conversion of $CH_3Br$, and reaction parameters, T, P, and τ (space time), where τ was calculated according to the equation: τ=reactor volume/incoming flow rate. Aromatic product distributions are underscored.

TABLE 1

| | Examples 4-15: $CH_3Br$ coupling over Ca-doped ZSM-5: Reaction parameters and products | | | | | | | | | | | | | |
|---|---|---|---|---|---|---|---|---|---|---|---|---|---|---|
| Ex. | Conv. % | T, °C. | P, bar | τ, sec | C1 | C2 | C3 | C4 | C5 | C6 | C7 | C8 | C9 | C10 |
| 4 | 65 | 225 | 5 | 60 | 0.4 | 0.2 | 5.8 | 21.8 | 18.8 | 14.5 | 11.7 | 12.8 | 5.8 | 4.2 |
| 5 | 90 | 250 | 5 | 6 | 0.5 | 0.4 | 6.1 | 30.2 | 22.5 | 18.3 | 12.3 | 7.6 | 2.1 | |
| 6 | 95 | 250 | 5 | 20 | 0.3 | 0.3 | 6.9 | 22.4 | 20.2 | 16.3 | 13.5 | 12.7 | 5.6 | 2.1 |
| 7 | 97 | 250 | 5 | 60 | 0.4 | 0.3 | 5.6 | 19.9 | 18.5 | 15.2 | 13.2 | 13.0 | 8.4 | 5.6 |
| 8 | 97 | 250 | 1 | 12 | 0.2 | 0.2 | 6.1 | 21.4 | 21.5 | 18.5 | 14.0 | 9.7 | 6.0 | 2.2 |
| 9 | 95 | 275 | 5 | 6 | 0.4 | 0.7 | 9.9 | 27 | 20.7 | 18.2 | 13.5 | 7.6 | 2.1 | |
| 10 | 100 | 275 | 3 | 50 | 1.8 | 2 | 4.4 | 16.2 | 18.2 | 16.1 | 13.8 | 12.5 | 6.3 | 2.5 |
| | | | | | | | | | | | _0.9_ | _1.6_ | _2.5_ | _1.2_ |
| 11 | 97 | 300 | 5 | 6 | 0.5 | 0.8 | 11.4 | 26.5 | 19.6 | 17 | 13.3 | 8.2 | 2.6 | |
| 12 | 100 | 350 | 3 | 8 | 1.0 | 1.5 | 14.6 | 26.7 | 19.4 | 15.2 | 10.1 | 6.2 | 2.8 | 0.8 |
| | | | | | | | | | | | _0.6_ | _1.3_ | _0.9_ | _0_ |
| 13 | 100 | 350 | 3 | 16 | 1.0 | 2.0 | 11.9 | 25.2 | 19.1 | 13.8 | 9.4 | 6.9 | 2.6 | 0.0 |
| | | | | | | | | | | | _1.6_ | _4.5_ | _2.1_ | _0.9_ |
| 14 | 100 | 350 | 3 | 50 | 1.1 | 2.2 | 15.5 | 25.4 | 14.6 | 9.1 | 5.4 | 3.2 | 0.8 | 0.0 |
| | | | | | | | | | | | _4.6_ | _10.8_ | _4.9_ | _3.4_ |
| 15 | 100 | 350 | 3 | 100 | 1.2 | 1.9 | 16.7 | 19.8 | 10.5 | 7.8 | 3.6 | 2.3 | 0.9 | 0.0 |
| | | | | | | | | | | | _8.4_ | _17.7_ | _9.2_ | _1.1_ |

As seen in Table 1, an alkaline-earth metal-doped zeolite facilitated the conversion of a brominated alkane ($CH_3Br$) into a number of different hydrocarbons, including linear and branched alkanes, olefins, and aromatic compounds. Water was also produced, as a byproduct of HBr neutralization. GC analysis of products showed high conversions of methyl bromide (with lower conversions occurring at low temperatures, and higher conversions occurring at high temperatures), and pH measurements showed complete neutralization of HBr formed in the reaction.

In general, the percentage of $C_5$ and higher hydrocarbons produced for a given run exceeded 70%, and the percentage of $C_6$ and higher hydrocarbons produced exceeded 50%. Detected aromatic compounds include toluene ($C_7$), xylenes and ethylbenzene ($C_8$), mesitylenes and ethylmethylbenzene ($C_9$), and higher hydrocarbons (e.g., $C_{10}$). In some runs, a small amount of benzene was detected.

Although not bound by theory, the carbon-carbon coupling appears to proceed in two stages, similar to what is observed with the formations of hydrocarbons from methanol coupling. In a first, rapid stage, olefins appear to form, couple, and then crack. This appears to be followed by a slower, second stage yielding aromatic products and paraffins after longer exposure to the catalyst and higher temperatures.

It has been observed that freshly prepared solid cataloreactant does not give the "steady state" product distribution obtained after 1 cycle (an repeated for a number of additional cycles) of coupling/bromine sequestering, followed by solid reoxygenation and bromine release. That is, "first run" product distributions are dissimilar from the distributions seen using recycled solid cataloreactant.

EXAMPLES 16-18

To demonstrate that lighter hydrocarbons can be recycled into the coupling reactor, first propylene (4.5 mmol), and then a mixture of $CH_3Br$ and propylene (3:1 v/v or 3.3 mmol:1.1 mmol) were utilized as a feed in a glass reaction tube configured as described in Examples 4-15. The product distribution was compared to that obtained using $CH_3Br$ (4.5 mmol) alone. The results are presented in Table 2. Aromatic product distributions are underscored.

TABLE 2

Examples 16-18: Reaction products for propylene (Ex. 16); 3:1 CH3Br:propylene (Ex. 17); and CH₃Br alone (Ex. 18) over Ca-doped ZSM-5.

| Ex. | Conv. % | T, °C. | P, bar | τ, sec | $C_1$, sel | $C_2$ | $C_3$ | $C_4$ | $C_5$ | $C_6$ | $C_7$ | $C_8$ | $C_9$ | $C_{10}$ |
|---|---|---|---|---|---|---|---|---|---|---|---|---|---|---|
| 16 | n.a. | 325 | 3 | 16 | 0.1 | 0.6 | 9.7 | 16.3 | 21.0 | 18.1 | 13.8 | 9.9 | 6.3 | 2.5 |
|    |      |     |   |    |     |     |     |      |      |      | _0.4_ | _0.5_ | _0.6_ | _0.4_ |
| 17 | 100 | 300 | 3 | 16 | 0.2 | 0.5 | 8.3 | 18.4 | 19.0 | 16.7 | 14.2 | 10.9 | 7.0 | 3.2 |
|    |      |     |   |    |     |     |     |      |      |      | _0.3_ | _0.5_ | _0.4_ | _0.3_ |
| 18 | 95  | 300 | 3 | 16 | 0.5 | 0.6 | 8.6 | 23.7 | 19.3 | 16.2 | 12.8 | 9.3 | 5.7 | 1.9 |

Table 2 shows that the less desirable (from the standpoint of gasoline production) light olefins may be recycled into the feed stream for incorporation into heavier products. The fact that the product distribution for a propylene feed is similar to that for MeBr and MeBr/propylene 1:1 (C:C basis) shows that recycling of light olefins will improve the overall yield of gasoline products.

The invention has been described by reference to various examples and preferred embodiments, but is not limited thereto. Other modifications and substitutions can be made without departing from the scope of the invention. For example, the oligomerization processes described herein are also intended to encompass halogenation of olefin feedstocks using a hydrogen halide (e.g., HBr) or molecular halogen; halogenation of acetylenes (alkynes) using hydrogen halide or molecular halogen; halogenation of alcohols or ethers using hydrogen halide or molecular halogen; and halogenation of alkanes using molecular halogen and a catalyst that controls the halogenation. Specifically, the catalyst may control one or both of the degree of halogenation (number of halogens per molecule) and the position of halogenation (e.g. terminal vs. internal halogenation for a long chain alkane). Other modifications may be made as well. The invention is limited only by the appended claims and equivalents thereof.

What is claimed is:

1. A method of making a product hydrocarbon having a carbon number $C_n$, where $n \geq 2$, comprising:
   reacting a halogenating agent with a reactant hydrocarbon having a carbon number $C_m$, where $m<n$, to form a halogenated hydrocarbon;
   contacting the halogenated hydrocarbon with a metal-oxygen cataloreactant to form hydrogen halide and a plurality of product hydrocarbons, wherein at least a portion of the product hydrocarbons have a carbon number $C_n$, where $n \geq 2$, and wherein at least 50% of the product hydrocarbons are $C_6$ or higher hydrocarbons or at least 70% of the product hydrocarbons are $C_5$ or higher hydrocarbons;
   trapping halogen from the hydrogen halide with the metal-oxygen cataloreactant;
   recovering the product hydrocarbons; and
   regenerating the metal-oxygen cataloreactant to recover the halogen.

2. The method of claim 1, wherein at least 50% of the product hydrocarbons are $C_6$ or higher hydrocarbons.

3. The method of claim 1, wherein at least 70% of the product hydrocarbons are $C_5$ or higher hydrocarbons.

4. The method of claim 1, wherein at least 50% of the product hydrocarbons are $C_6$ or higher hydrocarbons and at least 70% of the product hydrocarbons are $C_5$ or higher hydrocarbons.

5. The method of claim 1, wherein the reaction between the halogenating agent and the reactant hydrocarbon occurs at a reactant hydrocarbon-to-halogenating agent ratio of from 1:10 to 100:1 by volume.

6. The method of claim 1, wherein the reaction between the halogenating agent and the reactant hydrocarbon occurs at a temperature of from 20° C. to 900° C. and a pressure of from 0.1 atm to 200 atm.

7. The method of claim 1 further comprising recycling the halogen as the halogenating agent to react with the reactant hydrocarbon.

8. The method of claim 1 further comprising allowing any $C_1$ to $C_3$ hydrocarbons, which are formed from allowing the halogenated hydrocarbon to contact the first metal-oxygen cataloreactant, to contact the first metal-oxygen cataloreactant again to form one or more $C_4$ or higher hydrocarbons.

9. A method of making a product hydrocarbon having a carbon number $C_n$, where $n \geq 2$, comprising:
   reacting a halogenating agent with a reactant hydrocarbon having a carbon number $C_m$, where $m<n$, to form hydrogen halide and a halogenated hydrocarbon;
   contacting the halogenated hydrocarbon with a metal-oxygen cataloreactant to form a plurality of product hydrocarbons, wherein at least a portion of the product hydrocarbons have a carbon number $C_n$, where $n \geq 2$, and wherein at least 50% of the product hydrocarbons are $C_6$ or higher hydrocarbons or at least 70% of the product hydrocarbons are $C_5$ or higher hydrocarbons;
   trapping halogen from the hydrogen halide with the metal-oxygen cataloreactant;
   recovering the product hydrocarbons; and
   regenerating the metal-oxygen cataloreactant to recover the halogen.

10. The method of claim 9, wherein at least 50% of the product hydrocarbons are $C_6$ or higher hydrocarbons.

11. The method of claim 9, wherein at least 70% of the product hydrocarbons are $C_5$ or higher hydrocarbons.

12. The method of claim 9, wherein at least 50% of the product hydrocarbons are $C_6$ or higher hydrocarbons and at least 70% of the product hydrocarbons are $C_5$ or higher hydrocarbons.

13. The method of claim 9, wherein the reaction between the halogenating agent and the reactant hydrocarbon occurs at a reactant hydrocarbon-to-halogenating agent ratio of from 1:10 to 100:1 by volume.

14. The method of claim 9, wherein the reaction between the halogenating agent and the reactant hydrocarbon occurs at a temperature of from 20° C. to 900° C. and a pressure of from 0.1 atm to 200 atm.

15. A method of making a product hydrocarbon having a carbon number $C_n$, where $n \geq 2$, comprising:

reacting a halogenating agent with a reactant hydrocarbon having a carbon number $C_m$, where m<n, to form a halogenated hydrocarbon;

contacting the halogenated hydrocarbon with a first metal-oxygen cataloreactant to form a hydrogen halide and a plurality of product hydrocarbons having a carbon number $C_n$, where $n \geq 2$, at least 50% of which are $C_6$ or higher hydrocarbons or at least 70% of which are $C_5$ or higher hydrocarbons;

contacting the hydrogen halide with a second metal-oxygen cataloreactant to form a halogenated cataloreactant;

recovering the product hydrocarbons; and contacting the halogenated cataloreactant with oxygen or air to regenerate the cataloreactant and form a molecular halogen.

16. The method of claim 15, wherein at least 50% of the plurality of product hydrocarbons are $C_6$ or higher hydrocarbons.

17. The method of claim 15, wherein at least 70% of the plurality of product hydrocarbons are $C_5$ or higher.

18. The method of claim 15, wherein at least 50% of the plurality of product hydrocarbons are $C_6$ or higher and at least 70% of the plurality of product hydrocarbons are $C_5$ or higher.

19. The method of claim 15 further comprising: recycling the molecular halogen as the halogenating agent to react with the reactant hydrocarbon.

20. The method of claim 15 further comprising allowing any $C_1$ to $C_3$ hydrocarbons, which are formed from allowing the halogenated hydrocarbon to contact the first metal-oxygen cataloreactant, to contact the first metal-oxygen cataloreactant again to form one or more $C_4$ or higher hydrocarbons.

* * * * *